(12) United States Patent
Cai et al.

(10) Patent No.: US 11,050,951 B2
(45) Date of Patent: Jun. 29, 2021

(54) GUIDANCE SYSTEM FOR A NEAR-INFRARED FLUORESCEIN ANGIOGRAPHY OPERATION WITH A 785NM CONTINUOUS WAVELENGTH LIGHT SOURCE

(71) Applicant: Nanjing Nuoyuan Medical Devices Co., LTD., Jiangsu (CN)

(72) Inventors: Huiming Cai, Jiangsu (CN); Yiqing Wang, Jiangsu (CN)

(73) Assignee: Nanjing Nuoyuan Medical Devices Co., LTD., Nanjing (CN)

( * ) Notice: Subject to any disclaimer, the term of this patent is extended or adjusted under 35 U.S.C. 154(b) by 137 days.

(21) Appl. No.: 16/410,700

(22) Filed: May 13, 2019

(65) Prior Publication Data

US 2020/0120291 A1    Apr. 16, 2020

(30) Foreign Application Priority Data

Oct. 10, 2018 (CN) .......................... 201811182746.3

(51) Int. Cl.
*H04N 5/33* (2006.01)
*H04N 5/225* (2006.01)
(Continued)

(52) U.S. Cl.
CPC ............... *H04N 5/33* (2013.01); *A61B 1/043* (2013.01); *A61B 1/06* (2013.01); *H04N 5/2256* (2013.01)

(58) Field of Classification Search
CPC ... A61B 1/043; A61B 1/0638; A61B 1/00009; A61B 5/0071; A61B 5/0035;
(Continued)

(56) References Cited

U.S. PATENT DOCUMENTS 5,450,291 A * 9/1995 Kumagai ............... G03B 17/12
362/3
5,690,417 A * 11/1997 Polidor ............... G02B 21/084
359/387

(Continued)

FOREIGN PATENT DOCUMENTS

WO WO-2014124537 A1 * 8/2014 ............ A61B 5/742
WO WO-2018034075 A1 * 2/2018 ............ A61B 1/00
WO WO-2020066610 A1 * 4/2020 ............ A61B 1/06

*Primary Examiner* — David E Harvey
(74) *Attorney, Agent, or Firm* — Casimir Jones, S.C.; Brian F. Bradley

(57) ABSTRACT

A guidance system for a near-infrared fluorescein angiography operation with a 785 nm continuous wavelength light source is provided. The guidance system includes a near infrared continuous laser emitting source, a visible light illumination source, a light collector, a light splitter connected to the light collector, a visible light filter, a near infrared filter, a color camera connected to the light splitter via the visible light filter, a near infrared camera connected to the light splitter via the near infrared filter, a terminal display, and a shell configured to contact with the body tissue of the patient. The near infrared to continuous laser emitting source and the visible light illumination source are provided on a light source support in the shell. The shell is provided therein with a viewing channel which is connected to the light collector. Both the color camera and the near infrared camera are connected to the terminal display.

14 Claims, 2 Drawing Sheets

(51) Int. Cl.
*A61B 1/04* (2006.01)
*A61B 1/06* (2006.01)

(58) Field of Classification Search
CPC . A61B 2090/364; A61B 1/00096; A61B 1/06;
A61B 1/0607; H04N 5/332; H04N 5/33;
H04N 5/2256
See application file for complete search history.

(56) References Cited

U.S. PATENT DOCUMENTS

| | | | | | |
|---|---|---|---|---|---|
| 5,910,816 | A | * | 6/1999 | Fontenot | A61B 5/0059 348/162 |
| 6,008,889 | A | * | 12/1999 | Zeng | A61B 5/0059 356/318 |
| 6,033,087 | A | * | 3/2000 | Shozo | F21V 5/04 362/244 |
| 6,603,552 | B1 | * | 8/2003 | Cline | A61B 5/0071 356/417 |
| 7,429,117 | B2 | * | 9/2008 | Pohlert | H04N 5/2256 362/11 |
| 7,602,563 | B2 | * | 10/2009 | Bloch | H04N 5/2256 219/121.67 |
| 7,986,473 | B2 | * | 7/2011 | Bloch | G02B 7/008 359/820 |
| 9,345,389 | B2 | * | 5/2016 | Nie | A61B 90/37 |
| 9,451,882 | B2 | * | 9/2016 | Nie | A61B 5/06 |
| 9,642,532 | B2 | * | 5/2017 | Fengler | A61B 1/0638 |
| 2005/0182434 | A1 | * | 8/2005 | Docherty | A61B 1/043 606/170 |
| 2005/0225977 | A1 | * | 10/2005 | Amphlett | G03B 15/03 362/230 |
| 2006/0152586 | A1 | * | 7/2006 | Komiya | G01J 3/0218 348/207.99 |
| 2007/0046778 | A1 | * | 3/2007 | Ishihara | G01N 21/6456 348/68 |
| 2007/0161907 | A1 | * | 7/2007 | Goldman | A61M 5/427 600/476 |
| 2008/0147053 | A1 | * | 6/2008 | Kang | G01N 21/6456 606/9 |
| 2009/0137908 | A1 | * | 5/2009 | Patwardhan | A61B 5/0071 600/476 |
| 2009/0236541 | A1 | * | 9/2009 | Lomnes | A61B 1/05 250/458.1 |
| 2011/0104071 | A1 | * | 5/2011 | Lee | A61B 5/0084 424/9.6 |
| 2012/0277559 | A1 | * | 11/2012 | Kohl-Bareis | A61B 5/0261 600/324 |
| 2012/0326055 | A1 | * | 12/2012 | Wilson | G01J 3/4406 250/459.1 |
| 2013/0250242 | A1 | * | 9/2013 | Cheng | A61B 3/14 351/207 |
| 2014/0171764 | A1 | * | 6/2014 | Kim | A61B 1/043 600/317 |
| 2014/0378843 | A1 | * | 12/2014 | Valdes | G02B 21/36 600/476 |
| 2015/0282749 | A1 | * | 10/2015 | Zand | A61B 1/0005 600/301 |
| 2015/0297086 | A1 | * | 10/2015 | Hong | G01N 21/6456 600/431 |
| 2015/0320385 | A1 | * | 11/2015 | Wright | A61B 8/485 600/474 |
| 2015/0381909 | A1 | * | 12/2015 | Butte | H04N 9/04 348/68 |
| 2016/0062103 | A1 | * | 3/2016 | Yang | A61B 1/042 250/552 |
| 2016/0262626 | A1 | * | 9/2016 | Pelosi | A61B 5/0077 |
| 2016/0287081 | A1 | * | 10/2016 | Yang | A61B 90/361 |
| 2017/0124768 | A1 | * | 5/2017 | Walle-Jensen | G06T 19/006 |
| 2017/0209050 | A1 | * | 7/2017 | Fengler | A61B 1/0684 |
| 2017/0316554 | A1 | * | 11/2017 | Nakamura | H04N 5/238 |
| 2018/0024341 | A1 | * | 1/2018 | Romanowski | G02B 21/365 359/385 |
| 2018/0146866 | A1 | * | 5/2018 | Chachisvilis | A61B 5/0261 |
| 2018/0279864 | A1 | * | 10/2018 | Frangioni | A61B 90/361 |
| 2018/0310829 | A1 | * | 11/2018 | Frangioni | A61B 5/0071 |
| 2019/0076005 | A1 | * | 3/2019 | Song | A61B 5/0044 |
| 2019/0133452 | A1 | * | 5/2019 | Sanchez | A61B 5/0079 |
| 2019/0203255 | A1 | * | 7/2019 | Auner | G01J 3/0291 |
| 2019/0209000 | A1 | * | 7/2019 | Treado | A61B 1/0646 |
| 2019/0343450 | A1 | * | 11/2019 | Park | A61B 5/0059 |
| 2019/0376892 | A1 | * | 12/2019 | Ishikawa | G01N 21/64 |
| 2019/0379840 | A1 | * | 12/2019 | Frangioni | A61B 1/0005 |

* cited by examiner

GUIDANCE SYSTEM FOR A NEAR-INFRARED FLUORESCEIN ANGIOGRAPHY OPERATION WITH A 785NM CONTINUOUS WAVELENGTH LIGHT SOURCE

CROSS REFERENCE TO RELATED APPLICATIONS

The present application claims the priority to the Chinese Patent Application (No. 201811182746.3), entitled "Guidance System for a Near-Infrared Fluorescein Angiography Operation with a 785 nm-Wavelength Light Source", filed with CNIPA on Oct. 10, 2018, the entirety of which is incorporated herein by reference.

TECHNICAL FIELD

The present application relates to the technical field of near infrared fluorescence imaging, and specifically to a guidance system for a near-infrared fluorescein angiography operation with a 785 nm continuous wavelength light source.

BACKGROUND ART

The method of marking biomolecules by radioactive tracers and fluorescent dyes has been successfully used in the field of biomedical research for years. However, in reality, in the field of imaging for physical clinical medicine, the application of a fluorescence probe in clinical research in most cases is limited to examination of tissue sections stained in vitro. Until later 1980s, some researchers tried to inject exogenous fluorescent dyes into the body of living beings as contrast media to distinguish pathological tissues from normal tissues during tumor detection by means of non-invasive or endoscopic optical measurement means. In recent years, the method of using fluorescent indicators as exogenous contrast media in in-vivo tumor imaging using near infrared has made great achievements.

In some technologies, when operating lymphadenectomy on living bodies (human bodies or animal bodies), the surgical staff often inject a fluorescent contrast medium into the blood. The contrast medium is absorbed by the lymph during blood circulation and in addition may also be excreted with the blood circulation after a period of time. When irradiated by near infrared rays, the contrast medium will emit near infrared light at a wave band different from the irradiating near infrared light. Then, with an ultra-high sensitive camera capable of collecting near infrared rays, viewing from a monitor, the surgical staff can correctly find the position of lymphatic tissue and thus is guided to operate lymphadenectomy properly.

However, the prior art only allows viewing and displaying the image of the blood region containing the fluorescent contrast medium, but does not allow displaying the image of those non-excited blood parts containing no fluorescent contrast medium. This leads the surgical staff to a situation that they can only see the condition of the lymphatic tissue in the irradiated part but not the condition of the overall operation area containing the lymphatic tissue. If they want to see the overall condition of the whole operation area, they need to shut off the irradiating continuous laser source. But in this case, they will not be able to see the position and the shape of the part they want to excise. Because of this, the surgical staff need to repeatedly switch between irradiating the near infrared light and removing the near infrared light, which is very inconvenient and causes trouble during operation.

Therefore, it becomes an important technical problem to be solved by those skilled in the art to provide a guidance system for a near-infrared fluorescein angiography operation with a 785 nm continuous wavelength light source, which is convenient to use.

SUMMARY

The purpose of the present application includes providing guidance system for a near-infrared fluorescein angiography operation with a 785 nm continuous wavelength light source to at least alleviate the technical problem of inconvenient use in the prior art.

The embodiments of the present application provide a guidance system for a near-infrared fluorescein angiography operation with a 785 nm continuous wavelength light source. The guidance system includes a near infrared continuous laser emitting source, a visible light illumination source, a light collector, a light splitter, a visible light filter, a near infrared filter, a color camera, a near infrared camera, a terminal display, and a shell configured to contact with the body tissue of the patient.

The shell is provided therein with a light source support. The near infrared continuous laser emitting source and the visible light illumination source are provided on the light source support. The shell is provided therein with a viewing channel. The viewing channel is connected to the light collector.

The light splitter is connected to the light collector. The color camera is connected to the light splitter via the visible light filter. The near infrared camera is connected to the light splitter via the near infrared filter.

Both the color camera and the near infrared camera are connected to the terminal display.

Optionally, a light blocking ring is provided below the near infrared continuous laser emitting source and the visible light illumination source. The light blocking ring is configured to contact with the body tissue of the patient. Optionally, the light blocking ring is provided below the viewing channel.

The axis of the light blocking ring coincides with the axis of the viewing channel.

Optionally, the light blocking ring is detachably connected to the viewing channel.

Optionally, the light blocking ring is in clamped on the outer sidewall of the viewing channel.

Optionally, the viewing channel is provided therein with a light filtering element which is configured to filter continuous laser.

Optionally, the viewing channel is provided therein with a connecting base. The light filtering element is detachably connected to the connecting base.

Optionally, the light filtering element is in clamping connection with the connecting base.

Optionally, the near infrared continuous laser emitting source has a wavelength ranging from 781 to 789 nm.

Optionally, the near infrared continuous laser emitting source has a wavelength of 785 nm.

Optionally, the light splitter which is configured to equally split the rays collected by the light collector into two identical light beams is connected to the light collector via optical fibers.

Optionally, the visible light filter allows passage of visible light with a wavelength range from 400 to 700 nm.

Optionally, the near infrared filter allows passage of infrared with a wavelength range from 770 to 800 nm.

Optionally, a video image capture card and an analysis system are further included.

Optionally, a light homogenizing plate is provided below the near infrared continuous laser emitting source and the visible light illumination source.

At least the following beneficial effects are provided.

The embodiments of the present application provide a guidance system for a near-infrared fluorescein angiography operation with a 785 nm continuous wavelength light source. The guidance system includes a near infrared continuous laser emitting source, a visible light illumination source, a light collector, a light splitter, a visible light filter, a near infrared filter, a color camera, a near infrared camera, a terminal display, and a shell configured to contact with the body tissue of the patient. The shell is provided therein with a light source support. The near infrared continuous laser emitting source and the visible light illumination source are provided on the light source support. The shell is provided therein with a viewing channel. The viewing channel is connected to the light collector. The light splitter is connected to the light collector. The color camera is connected to the light splitter via the visible light filter. The near infrared camera is connected to the light splitter via the near infrared filter. Both the color camera and the near infrared camera are connected to the terminal display. Two cameras are used to acquire the colored visible light image and the near infrared fluorescence image from the operation area at the same time and superimpose the fluorescence image subjected to processing directly to the colored visible light image in a particular color, so that the surgical staff may see the condition of both the whole operation area and the lymphatic tissue therein. This adapts to the viewing and thinking habits of the surgical staff most possibly, thus improves the operation efficiency and correctness. It is easy for surgical staff to use. And in use, the shell is in direct contact with the surface of the body tissue of the patient. In this way, the exciting light reflected by the surfaces of other body tissues will be blocked by the system itself, while the fluorescence produced when the exciting light which penetrates the skin or other body tissues irradiates ICG can pass through the viewing channel in the system center and be received by the light collector. This blocks the useless exciting light reflected from the surface of the skin or the body tissue back to the fluorescence detection device, prevents massive reflected exciting light from affecting the picture, improves the signal-to-noise ratio for the image and enhances the image effect.

The other features and advantages of the present application will be explained in the following description and will become apparent partially from the description or may be understood by implementing the present application.

The object and other advantages of the present application are achieved and obtained by the structure specifically indicated in the description, claims and figures.

To make the above object, features and advantages of the present application more apparent and understandable, preferred embodiments are specifically provided and detailed below with reference to the accompanied drawings.

BRIEF DESCRIPTION OF DRAWINGS

In order to more clearly explain the technical solutions in the specific embodiments of the present application or in the prior art, figures to be used in the description of the specific embodiments or the prior art will be briefly described. Obviously, the figures in the following description merely show some of the embodiments of the present application. Other figures may be obtained by those ordinarily skilled in the art based on these figures without paying creative efforts.

Reference signs: 1—shell; 11—light source support; 12—viewing channel; 121—light blocking ring; 122—light filtering element; 123—connecting base; 2—body tissue; 100—near infrared continuous laser emitting source; 200—visible light illumination source; 300—light collector; 400—light splitter; 500—visible light filter; 600—infrared filter; 700—color camera; 800—near infrared camera; 900—terminal display.

DETAILED DESCRIPTION OF EMBODIMENTS

Now the technical solutions of the present application will be clearly and completely described with reference to the figures. Apparently, the embodiments described are merely some but not all of the embodiments of the present application. All the other embodiments obtained by those ordinarily skilled in the art based on the embodiments provided in the present application without paying creative efforts shall fall within the scope of protection of the present application.

It should be appreciated that in the description of the present application, orientation or positional relations indicated by terms such as "center", "longitudinal", "transverse", "length", "width", "thickness", "upper", "lower", "front", "back", "left", "right", "vertical", "horizontal", "top", "bottom", "inner", "outer", "clockwise", "counterclockwise", "axial", "radial" and "circumferential" are the orientation or positional relations shown based on the figures, only for facilitating and simplifying description of the present application, rather than indicating or implying that the referred devices or elements must be in a particular orientation or constructed or operated in the particular orientation, and therefore they should not be construed as limiting the present application.

In addition, terms such as "first" and "second" are only configured to be descriptive and cannot be interpreted as indicating or implying relative importance or implicitly showing the number of the technical features referred to. Hence, features defined with "first" and "second" can explicitly or implicitly include one or more of such features. In the description of the present application, the term "a plurality of" means two or more, unless otherwise explicitly and specifically defined.

It should also be noted that, in the present application, terms such as "mount", "coupled", "connected" and "fixed" should be interpreted in a broad sense, unless otherwise explicitly specified and defined. For example, a connection could be fixed, detachable, or integrated, or it could be mechanical or electrical, or it could be direct or done via an intermediate medium indirectly, or it could be internal communication or interaction between two elements. Those ordinarily skilled in the art can understand the specific meaning of the above terms in the present application according to specific circumstances.

Now the present application will be further detailed by specific examples with reference to the figures.

Figure 1:
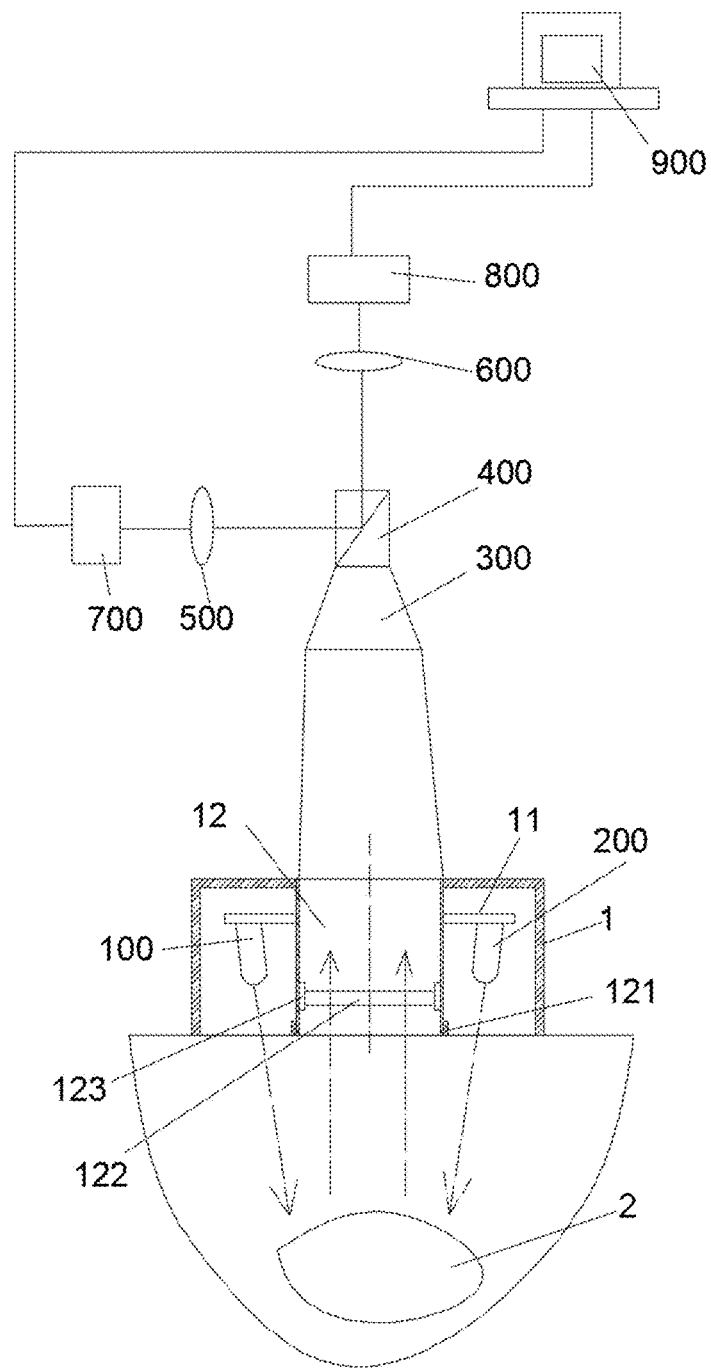
FIG. 1 is a structural schematic diagram of a guidance system for a near-infrared fluorescein angiography operation with a 785 nm continuous wavelength light source provided by an embodiment of the present application.
Figure 2:
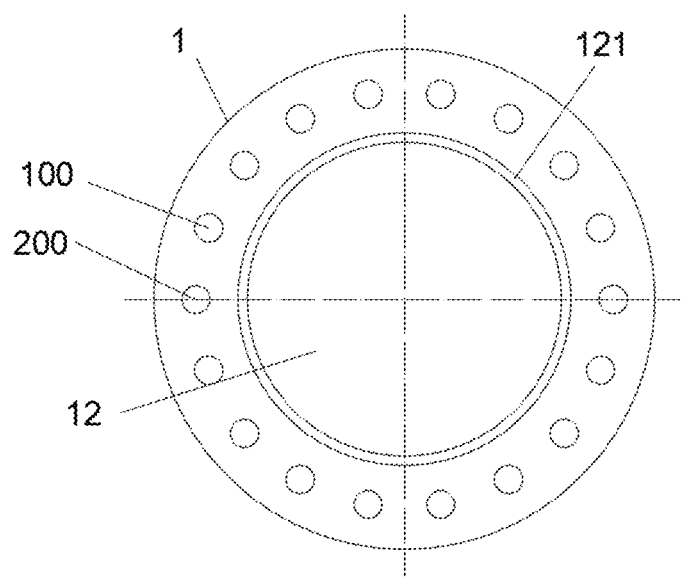
FIG. 2 is a bottom view of a shell of a guidance system for a near-infrared fluorescein angiography operation with a 785 nm continuous wavelength light source provided by an embodiment of the present application.

Reference is made to FIG. 1-FIG. 2.

The embodiments of the present application provide a guidance system for a near-infrared fluorescein angiography operation with a 785 nm continuous wavelength light source. The guidance system includes a near infrared continuous laser emitting source 100, a visible light illumination source 200, a light collector 300, a light splitter 400, a visible light filter 500, a near infrared filter 600, a color camera 700, a near infrared camera 800, a terminal display 900, and a shell 1 configured to contact with the body tissue 2 of the patient. The shell 1 is provided therein with a light source support 11. The near infrared continuous laser emitting source 100 and the visible light illumination source 200 are provided on the light source support 11. The shell 1 is provided therein with a viewing channel 12. The viewing channel 12 is connected to the light collector 300. The light splitter 400 is connected to the light collector 300. The color camera 700 is connected to the light splitter 400 via the visible light filter 500. The near infrared camera 800 is connected to the light splitter 400 via the near infrared filter 600. Both the color camera 700 and the near infrared camera 800 are connected to the terminal display 900.

An embodiment of the present application provides a guidance system for a near-infrared fluorescein angiography operation with a 785 nm continuous wavelength light source. The guidance system includes a near infrared continuous laser emitting source 100, a visible light illumination source 200, a light collector 300, a light splitter 400, a visible light filter 500, a near infrared filter 600, a color camera 700, a near infrared camera 800, a terminal display 900, and a shell 1 configured to contact with the body tissue 2 of the patient. The shell 1 is provided therein with a light source support 11. The near infrared continuous laser emitting source 100 and the visible light illumination source 200 are provided on the light source support 11. The shell 1 is provided therein with a viewing channel 12. The viewing channel 12 is connected to the light collector 300. The light splitter 400 is connected to the light collector 300. The color camera 700 is connected to the light splitter 400 via the visible light filter 500. The near infrared camera 800 is connected to the light splitter 400 via the near infrared filter 600. Both the color camera 700 and the near infrared camera 800 are connected to the terminal display 900. Two cameras are used to acquire the colored visible light image and the near infrared fluorescence image from the operation area at the same time and superimpose the fluorescence image subjected to processing directly to the colored visible light image in a particular color, so that the surgical staff may see the condition of both the whole operation area and the lymphatic tissue therein. This adapts to the viewing and thinking habits of the surgical staff most possibly, thus improves the operation efficiency and correctness. It is easy for surgical staff to use. And in use, the shell 1 is in direct contact with the surface of the body tissue 2 of the patient. In this way, the exciting light reflected by the surfaces of other body tissues 2 will be blocked by the system itself, while the fluorescence produced when the exciting light which penetrates the skin or other body tissues 2 irradiates ICG can pass through the viewing channel 12 in the system center and be received by the light collector 300. This blocks the useless exciting light reflected from the surface of the skin or the body tissue 2 back to the fluorescence detection device, prevents massive reflected exciting light from affecting the picture, improves the signal-to-noise ratio for the image and enhances the image effect.

Specifically, a light blocking ring 121 is provided below the light source. In use, the light blocking ring 121 is in direct contact with the surface of the skin or the body tissue 2 of the patient. That is to say, the light blocking strip is against the surface of the skin and the surface of the body tissue 2. In this way, to all the reflected light caused by that the exciting light irradiates to the surface of the skin and the body tissue 2 is blocked by the shell 1 and the light blocking ring 121, while the fluorescence emitted by the body tissue 2 may be collected by the light collector 300. Compared with traditional devices, it significantly reduces the continuous laser reflected into the lenses of the fluorescence detection device, and improves the contrast ratio of the picture and the observation depth. By providing the light filtering element 122 which filters continuous laser, the contrast ratio of the picture can further be improved.

The fluorescence detection device in the prior art should be 5-30 cm away from the patient in use. The light source is on the same plane with the fluorescence detection device. When irradiating the skin, part of the continuous laser penetrates the skin and reaches the corresponding body tissue 2 that contains a fluorescent agent which will emit fluorescence when irradiated by the exciting light. In this case, both the continuous laser reflected by the surface of the skin and the fluorescence emitted by the fluorescent agent will be received to the observing fluorescence detection device. Even when a light filtering element 122 is provided to block the exciting light, the presence of exciting light cannot be eliminated completely, which will have certain interference on the picture.

In an alternative of the present embodiment, a light blocking ring 121 is provided below the viewing channel 12. The axis of the light blocking ring 121 coincides with the axis of the viewing channel 12.

In this case, the light blocking ring 121 may be detachably connected to the viewing channel 12 in any suitable way, e.g. by clamping or threaded connection.

In an alternative of the present embodiment, the light blocking ring 121 is sleeved and clamped on the outer sidewall of the viewing channel 12, so as to be easily dismounted and mounted.

In an alternative of the present embodiment, the viewing channel 12 is provided therein with a light filtering element 122 configured to filter continuous laser.

In an alternative of the present embodiment, the viewing channel 12 is provided therein with a connecting base 123. The light filtering element is detachably connected to the connecting base 123. The connection could be made in any suitable way, e.g. by clamping or threaded connection.

Specifically, the viewing channel 12 is provided therein with a light filtering element 122. By filtering the continuous laser with a wavelength between 781 and 789 nm by the light filtering element 122, the fluorescence imaging effect is further improved.

In an alternative of the present embodiment, the near infrared continuous laser emitting source 100 has a wavelength between 781 and 789 nm.

In an alternative of the present embodiment, the near infrared continuous laser emitting source 100 has a wavelength of 785 nm.

By irradiating ICG with the continuous laser at a continuous laser wavelength between 781 and 789 nm, it is allowed to improve the fluorescent effect of the fluorescence and further improve the image effect.

Specifically, a light homogenizing plate is provided below the near infrared continuous laser emitting source 100 and the visible light illumination source 200, so as to homogenize the irradiation intensity that the near infrared continuous laser emitting source 100 and the visible light illumination source 200 apply to the affected part of the patient, and thus avoid intensive irradiation on some part from affecting the subsequent imaging.

In an alternative of the present embodiment, the light splitter 400 which is configured to equally split the rays collected by the light collector 300 into two identical light beams is connected to the light collector 300 via optical fibers. In an alternative of the present embodiment, the visible light filter 500 allows passage of visible light with a wavelength range from 400 to 700 nm.

In an alternative of the present embodiment, the near infrared filter 600 allows passage of infrared rays with a wavelength range from 770 to 800 nm. In an alternative of the present embodiment, the guidance system for a near-infrared fluorescein angiography operation with a 785 nm continuous wavelength light source further includes a video image capture card and an analysis system.

The guidance system for a near-infrared fluorescein angiography operation with a 785 nm continuous wavelength light source provided by the present embodiment is used in excision or inactivation operation to indicate the position of the part to be excised, e.g. lymph, wherein the near infrared continuous laser emitting source 100 emits near infrared continuous laser with a wavelength of 785 nm. When the near infrared continuous laser irradiates the surface of the subject to be operated that has absorbed indocyanine green (ICG) containing blood, the ICG is excited to emit 840 nm near infrared light. The visible light present in the operation environment will produce reflected light and scattered light when irradiating the body to be operated. The rays which blend 785 nm near infrared light, 840 nm near infrared light and visible light are split by the light splitter into two identical light beams which reach the visible light filter 500 and the near infrared filter 600. The near infrared filtering element 122 allows passage of near infrared light with a central wavelength of 840 nm and a bandwidth at 20 nm waveband. The visible light filtering element 122 allows passage of visible light with a wavelength range from 400 nm to 700 nm. The camera converts the optical signal into an electrical video signal and then is connected to the terminal display 900, and is also connected to the video signal input end of the analysis system for the video image capture card built therein to convert the analog video signal into digital image data. The digital image data is stored, recorded, computed, analyzed and reported by way of software.

With the guidance system for a near-infrared fluorescein angiography operation with a 785 nm continuous wavelength light source provided by the present embodiment, one is allowed to see a blended image of the lymphatic tissue to be excised, which is formed by superimposing the real colored image of the body to be operated. It is intuitional for one to find the exact position of the lymphatic tissue on the body to be operated and see its shape, and allows conveniently guiding the surgical staff to efficiently and precisely perform excision or inactivation operation and to make record before, after and during the operation.

In the description of the present specification, such description as reference terms "an embodiment", "some embodiments", "example", "specific example" or "some examples" means that the specific features, structures, materials or characteristics described with reference to such embodiment(s) or example(s) are included in at least one embodiment or example of the present application. In the present specification, schematic expressions of the above terms do not necessarily refer to the same embodiment or example. And the specific features, structures, materials or characteristics as described may be combined in any appropriate way in any one or more embodiments or examples. Further, those skilled in the art may incorporate and combine different embodiments or examples and the features in different embodiments or examples as described herein as long as they are not contradictory to one another.

Although the embodiments of the present application are already illustrated and described in the above, it should be appreciated that the above embodiments are exemplary, but should not be construed as limiting the present application. Those ordinarily skilled in the art may make changes, modifications, replacements and variations to the above embodiments within the scope of the present application.

INDUSTRIAL APPLICABILITY

The guidance system for a near-infrared fluorescein angiography operation with a 785 nm continuous wavelength light source provided by the embodiments of the present application most possibly adapts to the viewing and thinking habits of surgical staff, improves the operation efficiency and correctness, is easy for surgical staff to use, prevents massive reflected exciting light from affecting the picture, improves the signal-to-noise ratio of the image and enhances the image effect.

The invention claimed is:

1. A guidance system for a near-infrared fluorescein angiography operation with a 785 nm continuous wavelength light source, comprising a near infrared continuous laser emitting source, a visible light illumination source, a light collector, a light splitter, a visible light filter, a near infrared filter, a color camera, a near infrared camera, a terminal display, and a shell configured to contact with a body tissue of a patient,
   wherein the shell is provided therein with a light source support, the near infrared continuous laser emitting source and the visible light illumination source are provided on the light source support, the shell is provided therein with a viewing channel, the viewing channel is connected to the light collector;
   the light splitter is connected to the light collector, the color camera is connected to the light splitter via the visible light filter, the near infrared camera is connected to the light splitter via the near infrared filter; and
   both the color camera and the near infrared camera are connected to the terminal display;
   wherein a light blocking ring, different than the shell, is provided below the near infrared continuous laser emitting source and the visible light illumination source, the light blocking ring is configured to contact with the body tissue of the patient.

2. The guidance system for a near-infrared fluorescein angiography operation with a 785 nm continuous wavelength light source according to claim 1, wherein the light blocking ring is provided below the viewing channel;
   an axis of the light blocking ring coincides with an axis of the viewing channel.

3. The guidance system for a near-infrared fluorescein angiography operation with a 785 nm continuous wavelength light source according to claim 2, wherein the light blocking ring is detachably connected to the viewing channel.

4. The guidance system for a near-infrared fluorescein angiography operation with a 785 nm continuous wavelength light source according to claim 3, wherein the light blocking ring is clamped on an outer sidewall of the viewing channel.

5. The guidance system for a near-infrared fluorescein angiography operation with a 785 nm continuous wavelength light source according to claim 1, wherein the viewing channel is provided therein with a light filtering element configured to filter continuous laser.

6. The guidance system for a near-infrared fluorescein angiography operation with a 785 nm continuous wavelength light source according to claim 5, wherein the viewing channel is provided therein with a connecting base, the light filtering element is detachably connected to the connecting base.

7. The guidance system for a near-infrared fluorescein angiography operation with a 785 nm continuous wavelength light source according to claim 6, wherein the light filtering element is in clamping connection with the connecting base.

8. The guidance system for a near-infrared fluorescein angiography operation with a 785 nm continuous wavelength light source according to claim 1, wherein the near infrared continuous laser emitting source has a wavelength between 781 and 789 nm.

9. The guidance system for a near-infrared fluorescein angiography operation with a 785 nm continuous wavelength light source according to claim 8, wherein the near infrared continuous laser emitting source has a wavelength of 785 nm.

10. The guidance system for a near-infrared fluorescein angiography operation with a 785 nm continuous wavelength light source according to claim 1, wherein the light splitter which is configured to equally split rays collected by the light collector into two identical light beams is connected to the light collector via optical fibers.

11. The guidance system for a near-infrared fluorescein angiography operation with a 785 nm continuous wavelength light source according to claim 1, wherein the visible light filter allows passage of visible light with a wavelength range from 400 to 700 nm.

12. The guidance system for a near-infrared fluorescein angiography operation with a 785 nm continuous wavelength light source according to claim 11, wherein the near infrared filter allows passage of infrared rays with a wavelength range from 770 to 800 nm.

13. The guidance system for a near-infrared fluorescein angiography operation with a 785 nm continuous wavelength light source according to claim 1, further comprising a video image capture card and an analysis system.

14. The guidance system for a near-infrared fluorescein angiography operation with a 785 nm continuous wavelength light source according to claim 1, wherein a light homogenizing plate is provided below the near infrared continuous laser emitting source and the visible light illumination source.

* * * * *